US012596070B1

(12) United States Patent　　(10) Patent No.:　US 12,596,070 B1

Pocock et al.　　(45) Date of Patent:　Apr. 7, 2026

(54) MONITORING CHLOROPHYLL FLUORESCENCE AND GREEN LIGHT REFLECTANCE TO DETECT PLANT STRESS

(71) Applicant: MJNN LLC, South San Francisco, CA (US)

(72) Inventors: Tessa Hilary Pocock, Laramie, WY (US); Matthew Robert Urschel, Laramie, WY (US)

(73) Assignee: MJNN LLC, South San Francisco, CA (US)

( * ) Notice: Subject to any disclaimer, the term of this patent is extended or adjusted under 35 U.S.C. 154(b) by 1023 days.

(21) Appl. No.: 17/574,388

(22) Filed: Jan. 12, 2022

Related U.S. Application Data

(60) Provisional application No. 63/250,671, filed on Sep. 30, 2021, provisional application No. 63/137,004, filed on Jan. 13, 2021.

(51) Int. Cl.
| | |
|---|---|
| *G01N 21/64* | (2006.01) |
| *G01N 21/01* | (2006.01) |
| *G01N 21/63* | (2006.01) |
| *G01N 21/84* | (2006.01) |
| *G01N 33/00* | (2006.01) |

(52) U.S. Cl.
CPC ......... *G01N 21/6428* (2013.01); *G01N 21/01* (2013.01); *G01N 21/84* (2013.01); *G01N 33/0098* (2013.01); *G01N 2021/635* (2013.01); *G01N 2021/8466* (2013.01); *G01N 2201/062* (2013.01); *G01N 2201/0696* (2013.01)

(58) Field of Classification Search
None
See application file for complete search history.

(56) References Cited

U.S. PATENT DOCUMENTS

| | | |
|---|---|---|
| 806,108 A | 12/1905 | Clark |
| 3,910,701 A | 10/1975 | Henderson |
| 6,563,122 B1 | 5/2003 | Ludeker |

(Continued)

FOREIGN PATENT DOCUMENTS

| | | |
|---|---|---|
| JP | 2004101196 A | 4/2004 |
| RU | 2199730 C2 | 2/2003 |

(Continued)

OTHER PUBLICATIONS

Translation of WO2008040875A1, Roger Jean-Michel, Apr. 10, 2008 (Year: 2008).*

(Continued)

*Primary Examiner* — Henry H Nguyen

(74) *Attorney, Agent, or Firm* — Almanac IP Advisors LLP

(57)　　　　　ABSTRACT

Methods and systems for remote detection of growth conditions of a plant species. In a particular implementation, the present invention provides improved techniques for identifying one or more stress conditions in plants, including without limitation, drought stress, temperature stress, salinity stress and other conditions in a plant species. An example implementation assesses both steady-state chlorophyll fluorescence and green light reflectance of a plant species in real-time. A controller may detect drought and/or other stress conditions by comparing the respective signal trajectories of observed chlorophyll fluorescence and green light reflectance.

12 Claims, 13 Drawing Sheets

(56) References Cited

U.S. PATENT DOCUMENTS

| | | | | |
|---|---|---|---|---|
| 8,061,080 B2 * | 11/2011 | Loebl | ................... | A01G 9/249 |
| | | | | 47/58.1 LS |
| 8,850,742 B2 | 10/2014 | Dube | | |
| 2001/0030742 A1 * | 10/2001 | Kramer | ............... | G01N 21/255 |
| | | | | 356/417 |
| 2005/0072935 A1 * | 4/2005 | Lussier | ............. | G01N 21/6486 |
| | | | | 250/458.1 |
| 2005/0098713 A1 * | 5/2005 | Holland | ................ | G01N 21/64 |
| | | | | 250/221 |
| 2010/0039804 A1 | 2/2010 | Budde | | |
| 2010/0111369 A1 * | 5/2010 | Lussier | ............. | G01N 21/6486 |
| | | | | 356/417 |
| 2010/0115830 A1 * | 5/2010 | Dube | ................ | G01N 21/6486 |
| | | | | 356/402 |
| 2010/0289411 A1 * | 11/2010 | Smits | .................... | H05B 45/22 |
| | | | | 315/297 |
| 2013/0308675 A1 * | 11/2013 | Sneed | ............... | G01N 33/0098 |
| | | | | 374/121 |
| 2019/0059202 A1 * | 2/2019 | Lorek | ................. | A01B 79/005 |

FOREIGN PATENT DOCUMENTS

| | | | | | |
|---|---|---|---|---|---|
| WO | 2000075642 A1 | 12/2000 | | | |
| WO | 2007105946 A2 | 9/2007 | | | |
| WO | WO-2008040875 A1 | * | 4/2008 | ........... | G01N 21/274 |

OTHER PUBLICATIONS

Schuerger et al., "Effects of artificial lighting on the detection of plant stress with spectral reflectance remote sensing in bioregenerative life support systems," Int'l Journal of Astrobiology—Apr. 2006.

Smith, "Phytochrome-Mediated Responses: Implications for Controlled Environment Research Facilities," International Lighting in Controlled Environments Workshop 1994.

Buschmann et al., "Reflectance spectra and images of green leaves with different tissue structure and chlorophyll content," Israel Journal of Plant Sciences Mar. 14, 2013.

Gitelson et al., "Relationships between leaf chlorophyll content and spectral reflectance and algorithms for non-destructive chlorophyll assessment in higher plant leaves," J. Plant Physiol. 160. 271-282 (2003).

Gitelson et al. "Signature Analysis of Leaf Reflectance Spectra: Algorithm Development for Remote Sensing of Chlorophyll," j. Plant PhysioL. vol. 148. pp. 494-500 (1996).

Lichtenthaler et al., "Non-Destructive Determination of Chlorophyll Content of Leaves of a Green and Aurea Mutant of Tobacco by Reflectance Measurements," J. Plant Physiol. vol. 148. pp. 483-493 (1996).

Lichtenthaler et al., "Plant Stress Detection by Reflectance and Fluorescence," (1998).

Massa et al., "Development and testing of an efficient LED intracanopy lighting design for minimizing Equivalent System Mass in an advanced life-support system," Gravitational and space biology bulletin: publication of the American Society for Gravitational and Space Biology • Jul. 2005.

Zur et al., "The Spectral Contribution of Carotenoids To Light Absorption and Reflectance in Green Leaves," (2000). Papers in Natural Resources. 272.

* cited by examiner

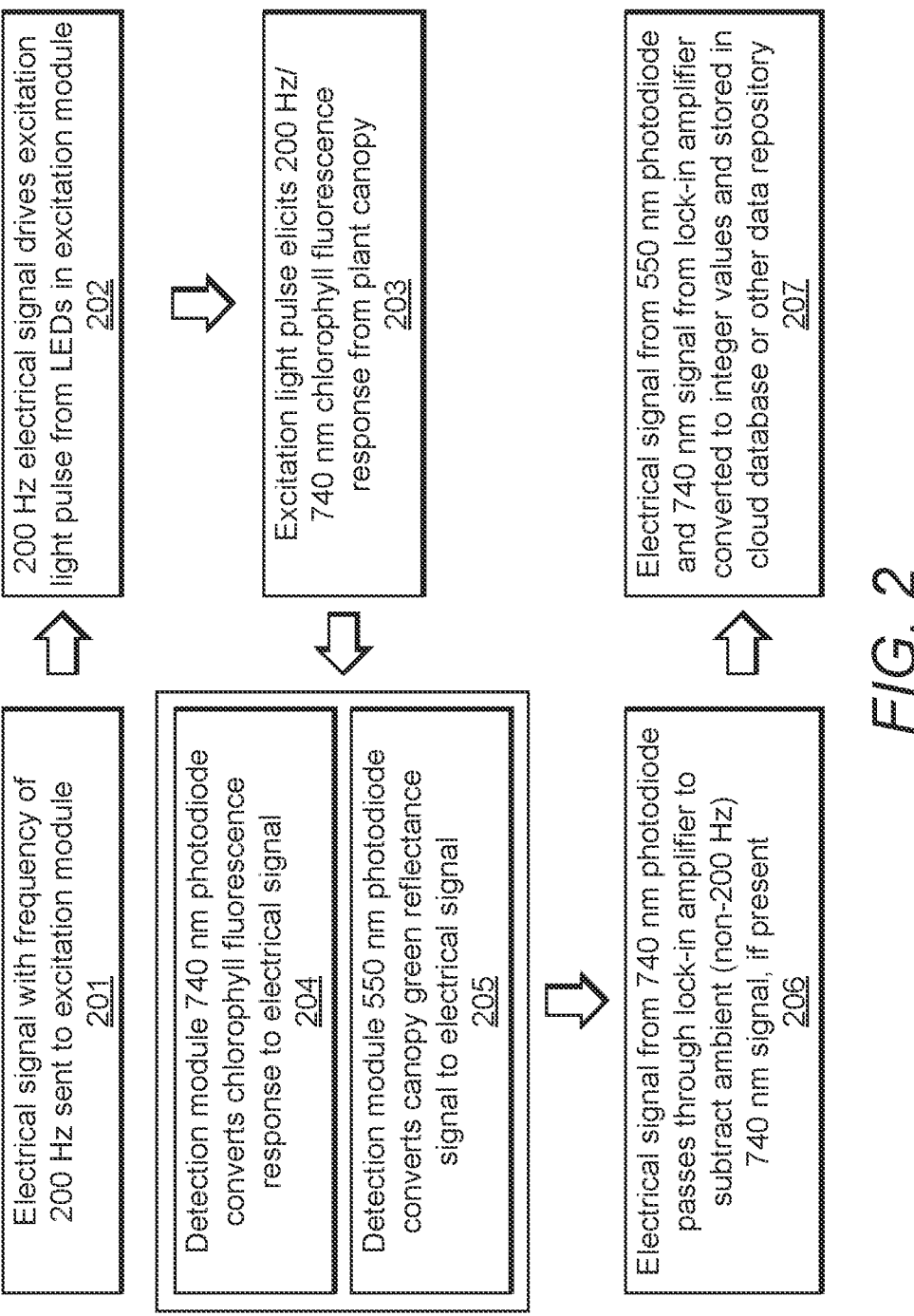

Electrical signal with frequency of 200 Hz sent to excitation module 201

200 Hz electrical signal drives excitation light pulse from LEDs in excitation module 202

Excitation light pulse elicits 200 Hz/740 nm chlorophyll fluorescence response from plant canopy 203

Detection module 740 nm photodiode converts chlorophyll fluorescence response to electrical signal 204

Detection module 550 nm photodiode converts canopy green reflectance signal to electrical signal 205

Electrical signal from 740 nm photodiode passes through lock-in amplifier to subtract ambient (non-200 Hz) 740 nm signal, if present 206

Electrical signal from 550 nm photodiode and 740 nm signal from lock-in amplifier converted to integer values and stored in cloud database or other data repository 207

MONITORING CHLOROPHYLL FLUORESCENCE AND GREEN LIGHT REFLECTANCE TO DETECT PLANT STRESS

CROSS-REFERENCE TO RELATED APPLICATIONS

The present application claims priority to U.S. provisional application Ser. No. 63/137,004 filed Jan. 13, 2021 and 63/250,671 filed Sep. 30, 2021, both of which are incorporated herein by reference for all purposes.

FIELD OF THE DISCLOSURE

The disclosure relates generally to the field of growth condition monitoring for plant species, and in particular to combining chlorophyll fluorescence and green light reflectance detection to improve detection of plant stress conditions.

BACKGROUND

Chlorophyll fluorescence is the re-emission by chlorophyll molecules of light energy absorbed from a light source. A non-stressed plant fluoresces approximately 1-3% of absorbed light but when stressed up to 30% of absorbed light can be re-emitted as chlorophyll fluorescence. Chlorophyll fluorescence is a widely studied indicator of photosynthetic performance in a variety of plant species. A number of chlorophyll fluorometers have been constructed to monitor chlorophyll fluorescence, including so-called "modulated excitation" fluorometers that remotely detect steady-state chlorophyll fluorescence. See Maxwell et al., Journal of Experimental Botany, Vol. 51, No. 345, pp. 659-668, April 2000 at pg. 660. In a modulated excitation fluorometer, a controller drives, during a measurement pulse, an excitation source with a periodic waveform (e.g., a square wave at a defined excitation frequency and duty cycle). A lock-in amplifier on the sensing end filters noise outside of the excitation frequency. See FIG. 1, below, of Schreiber et al., "New Ways of Assessing Photosynthetic Activity with a Pulse Modulation Fluorometer," at page 64 from Applications of Chlorophyll Fluorescence, H.K. Lichtenthaler (ed.), Kluwer Academic Publishers 1988).

SUMMARY OF THE DISCLOSURE

Embodiments of the disclosure are directed to methods and systems for remote detection of growth conditions of a plant species. In a particular implementation, the present invention provides improved techniques for identifying one or more stress conditions in plants, including without limitation, drought stress, temperature stress, salinity stress, pH stress and other conditions in a plant species. An example implementation assesses both steady-state chlorophyll fluorescence and green light reflectance of a plant species in real-time. A controller may detect drought and/or other stress conditions by statistically comparing trends in respective signal trajectories of observed chlorophyll fluorescence and, in some cases, green light reflectance.

BRIEF DESCRIPTION OF THE DRAWINGS

FIG. 2 is a flow chart illustrating an example process flow.

DETAILED DESCRIPTION

Figure 1:
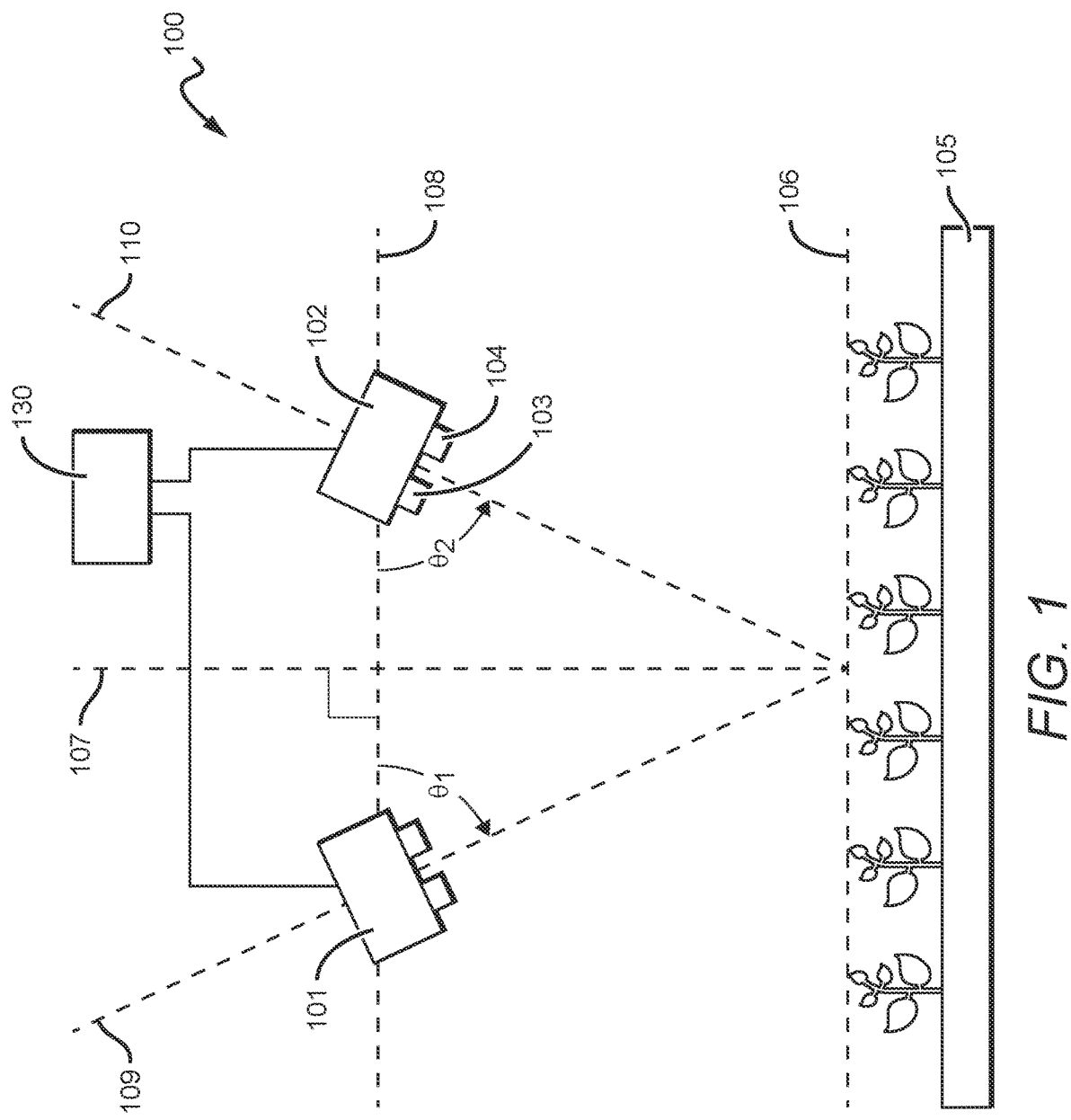
FIG. 1 is a functional diagram illustrating an example plant species monitoring system.

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, this disclosure is not intended to be limited to the disclosed embodiments, but is to be accorded the widest scope consistent with the claims and the principles and features disclosed herein.

The present disclosure describes a system for monitoring plant stress and other growth conditions of a plant species. In an example implementation, the system combines detection of steady-state chlorophyll a fluorescence and green light reflectance to provide an improved plant monitoring system generally and, in particular, a way of determining drought or other types of stress in a plant species. Some implementations can be configured to provide a farm production system with closed-loop control systems responsive to monitoring and analysis of chlorophyll a fluorescence (ChlF) and green light reflectance.

The system 100, in one implementation, has three main components: (1) a light excitation module 101 which delivers an excitation light pulse to the plant canopy 106 of a plant species 105, (2) a detection module 102 which senses and quantifies chlorophyll a fluorescence (ChlF) and green light reflectance, and (3) a microcontroller 130 which regulates the interval between the excitation pulses and records ChlF and green light reflectance data for analysis.

The excitation module 101, in one implementation, is a 3×4 array of royal blue (447 nm wavelength) light-emitting diodes (LEDs). The microcontroller 130 drives the excitation light source with a pulse-width modulated signal. Signal amplitude, frequency, duty cycle, pulse width and pulse interval are adjustable. In one example implementation, the microcontroller is configured to drive the LED array at 200 Hz, maximum amplitude and a 50% duty cycle. The length of the excitation pulse may be 0.8 seconds and the interval between pulses may be 15 minutes. In one implementation, the excitation module 101 is spaced at 17 inches from canopy 106. The photon flux density at crop level for the excitation pulses 600 $\mu$mol m$^{-2}$ s$^{-1}$ PAR. This parameter may be adjustable to 2500 $\mu$mol m$^{-2}$ s$^{-1}$ PAR or higher depending on crop type and other conditions.

The detection module 102 includes photodiodes to detect light at select wavelengths. In the implementation shown, the detection module 102 comprises a first photodiode 103 to detect light at the 740 nm wavelength and a second photodiode 104 to detect light at the 550 nm wavelength. Each photodiode, in one implementation, includes a near collimated optical filter to limit incoming light to the desired wavelengths and field of view. At 17 inches (43 cm) from the canopy, the field of view of the photodiodes, and thus the area of the plant canopy being sensed, was approximately 12 cm in diameter. In one implementation, a photodiode model 740-10-50 offered by Intor Inc. of Socorro, New Mexico can be used for the first photodiode 103. A photodiode model 530-10-50 offered by Intor Inc. of Socorro, New Mexico can be used for the second photodiode 104.

In the implementation shown, line 108 is the horizontal centerline of the excitation module 101 and the detection module 102. The distance between line 108 and the plant canopy 106 is approximately 43 cm or 17 inches. Line 109 represents the excitation module 101 center line relative to its field of view. Line 110 represents the detection module center line relative to the fields of view of the photodiodes 103 and 104. Lines 109 and 110 intersect at the plant canopy 106. In the implementation shown, excitation module 101 and detection module 102 are offset at an angle from horizontal center line 108 at respective angles ($\theta$1, $\theta$2) of 65 degrees. The foregoing dimensions are examples only and can vary considerably based on engineering and design considerations, as well as different crop/plant architectures.

The system 100 could be mounted at various points in a farm production system to monitor growth conditions of a plant species. For example, system 100 could be mounted at select locations of a grow line described in International Application Serial Nos. PCT/US19/023201 and PCT/US19/058770 to monitor the health of crops growing in a grow tower or other container.

FIG. 2 illustrates a data collection workflow according to one example implementation. In the implementation shown, the controller sends an electrical drive signal to excitation module 101 (201). As discussed above, the drive signal may be a signal having a frequency of 200 Hz, maximum amplitude and a 50% duty cycle. The pulse duration may be 0.8 seconds. The drive signal causes the excitation module 201 to emit the excitation light pulse (202). The excitation light pulse elicits a chlorophyll a fluorescence response from the canopy of the plant species (203). The first photodiode 103 of detection module 102 converts the detected chlorophyll a fluorescence response into an electrical signal (204). The second photodiode 104 of detection module 102 converts the detected green light reflectance of the canopy to an electrical signal (205). Measurement of green light reflectance does not require an excitation source and can rely on the grow light source provided it has a green light component. Changes in leaf anatomy will alter the amount of green light reflected from the plant. The electrical signals from the photodiode 103 pass through a lock-in amplifier to filter out any signal with a frequency other than 200 Hz (206). A low-pass filter and amplifier may also be used to substantially remove all harmonic signals. The controller 130 converts the electrical signals from the photodiodes 103, 104 into integer values and stores them in a cloud database or other repository for analysis (207). ChIF can be measured a plurality of times at each interval, such as 5 times. ChIF can be calculated as the average of multiple measurements (with low and high values omitted) during each pulse.

Green light reflectance and chlorophyll fluorescence can be monitored by repeating this data collection workflow at regular intervals, such as every fifteen (15) minutes. The time-correlated data can be stored in a data store and accessed by one or more analysis processes to monitor for and detect stress conditions.

Monitoring and correlating green light reflectance and chlorophyll fluorescence provides improvements to determining the growth and physiological states of various plant species. Particular implementations provide improved methods and systems for identifying drought stress in various plant species, such as kale, chard, arugula, lettuce, or any plant that contains chlorophyll a. As shown below, other types of stress conditions may also be detected.

Example 1—Drought Stress

Figure 3A:
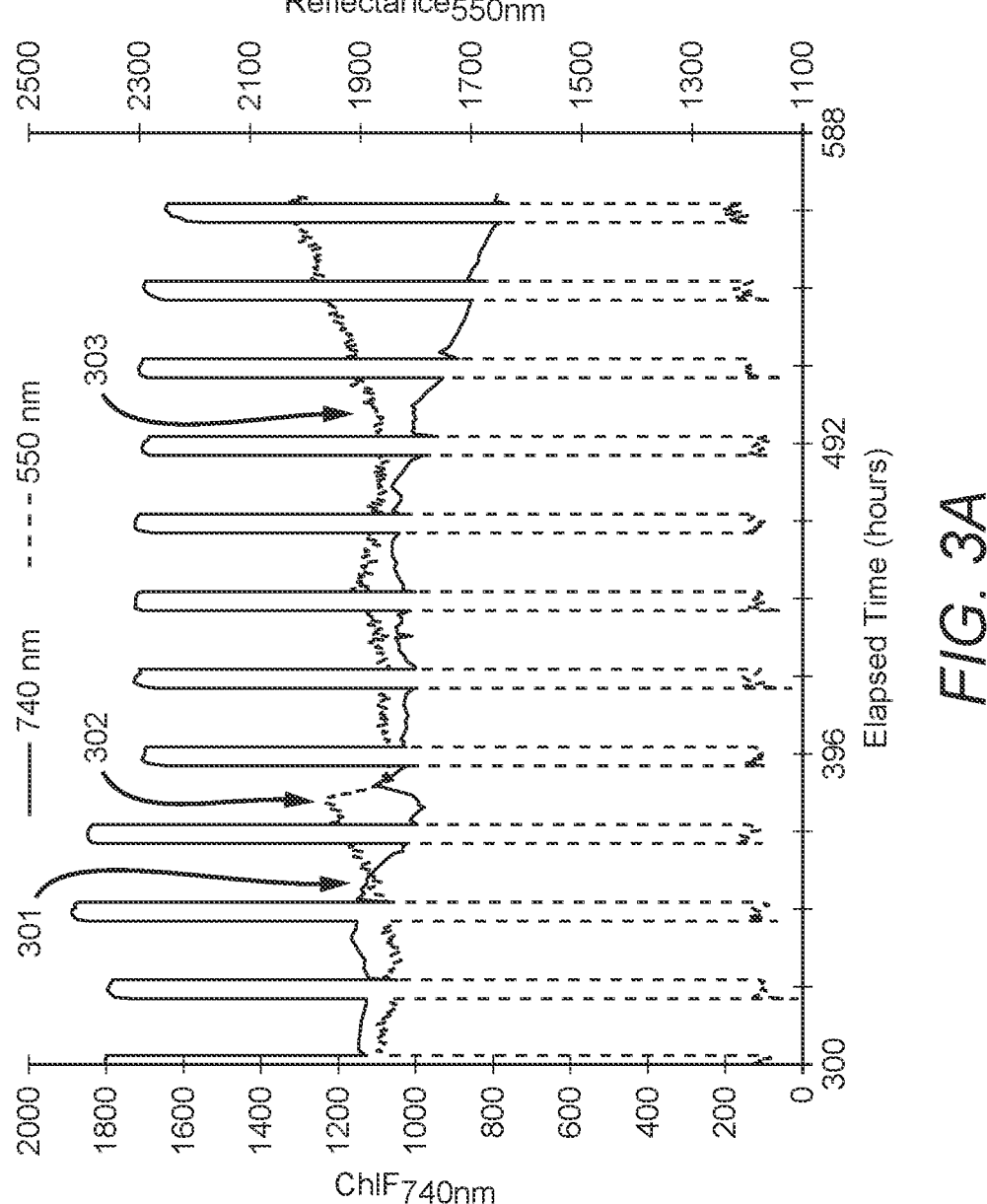
FIG. 3A plots observed chlorophyll fluorescence and green light reflectance over time for a plant species.
Figure 3B:
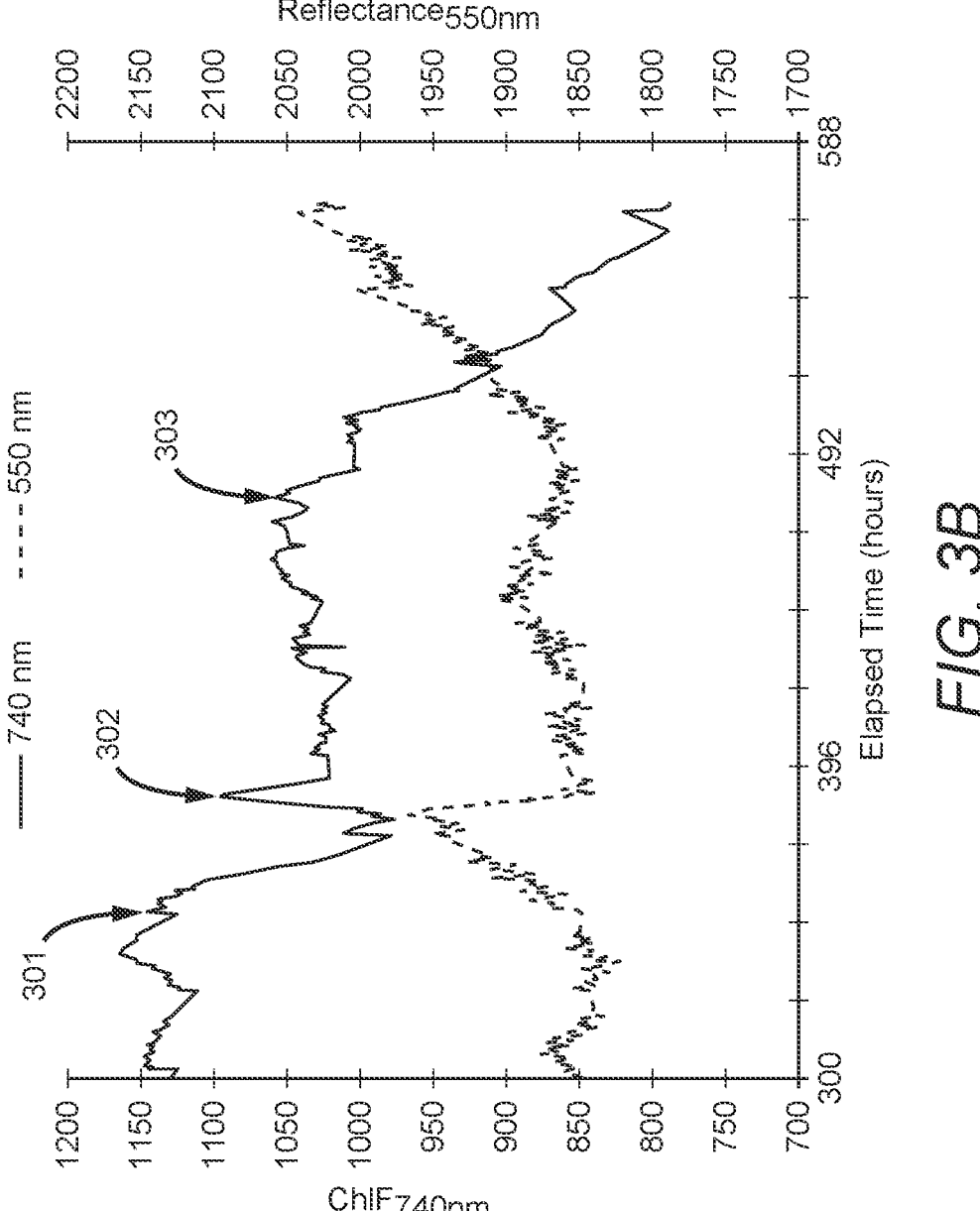
FIG. 3B omits the night-time data for didactic purposes.

FIGS. 3A and 3B plot observed ChIF and green light reflectance over time for a plant species growing under controlled environmental conditions, such as synthetic lighting and an automated irrigation system. Growth conditions for the experiment that generated the data in FIG. 3 were as follows: ~65° F. (18.3° C.), $CO_2$ concentration of ~400 ppm (ambient), relative humidity ~55-60%, light intensity 500 $\mu$mol m$^{-2}$ s$^{-2}$, 18 hour/6 hour light/dark period, spectral ratio of 20/20/60 percent blue/green/red. Plants were irrigated for 15 minutes once every other day with a nutrient solution prepared from reverse osmosis (RO) water and a commercial plant food product. The data observed in FIG. 3 involved artificially inducing drought stress in a plant species (here, a *Lactuca* or lettuce variety) and observing the relationship between ChIF and green light reflectance. Time point 301 represents the start of a detectable downturn in ChIF as a result of a first drought stress event where plant irrigation was turned off. Time point 302 represents the time when the plant species recovered from drought stress after irrigation resumed. Time point 303 represents a time point when drought stress conditions were reintroduced. The spikes in the ChIF and green reflectance data illustrated in FIG. 3A correspond to measurements taken during dark periods, where the grow lights were turned off. FIG. 3B omits the dark periods to facilitate analysis of the data.

Figure 4:
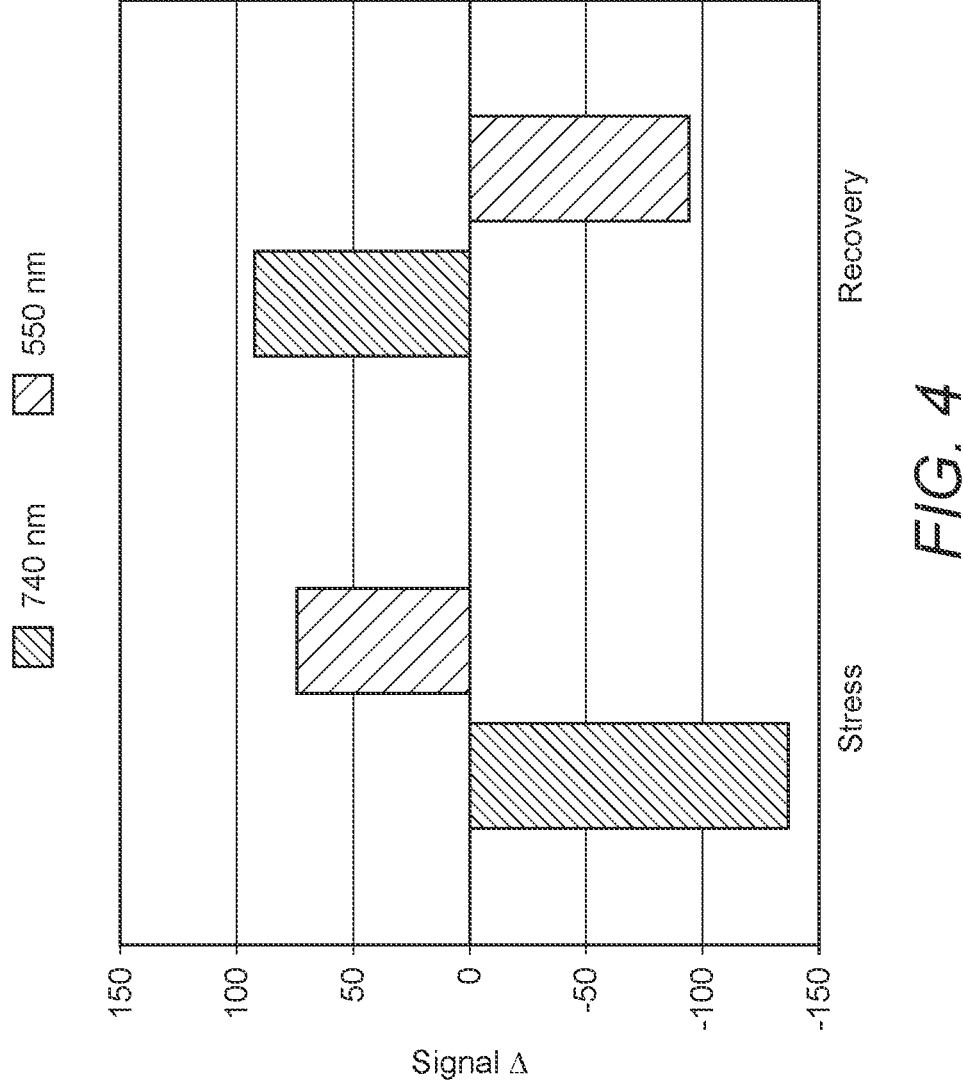
FIG. 4 is a bar graph illustrating the changes in observed chlorophyll fluorescence and green light reflectance for a plant species under stress and recovery.
Figure 5:
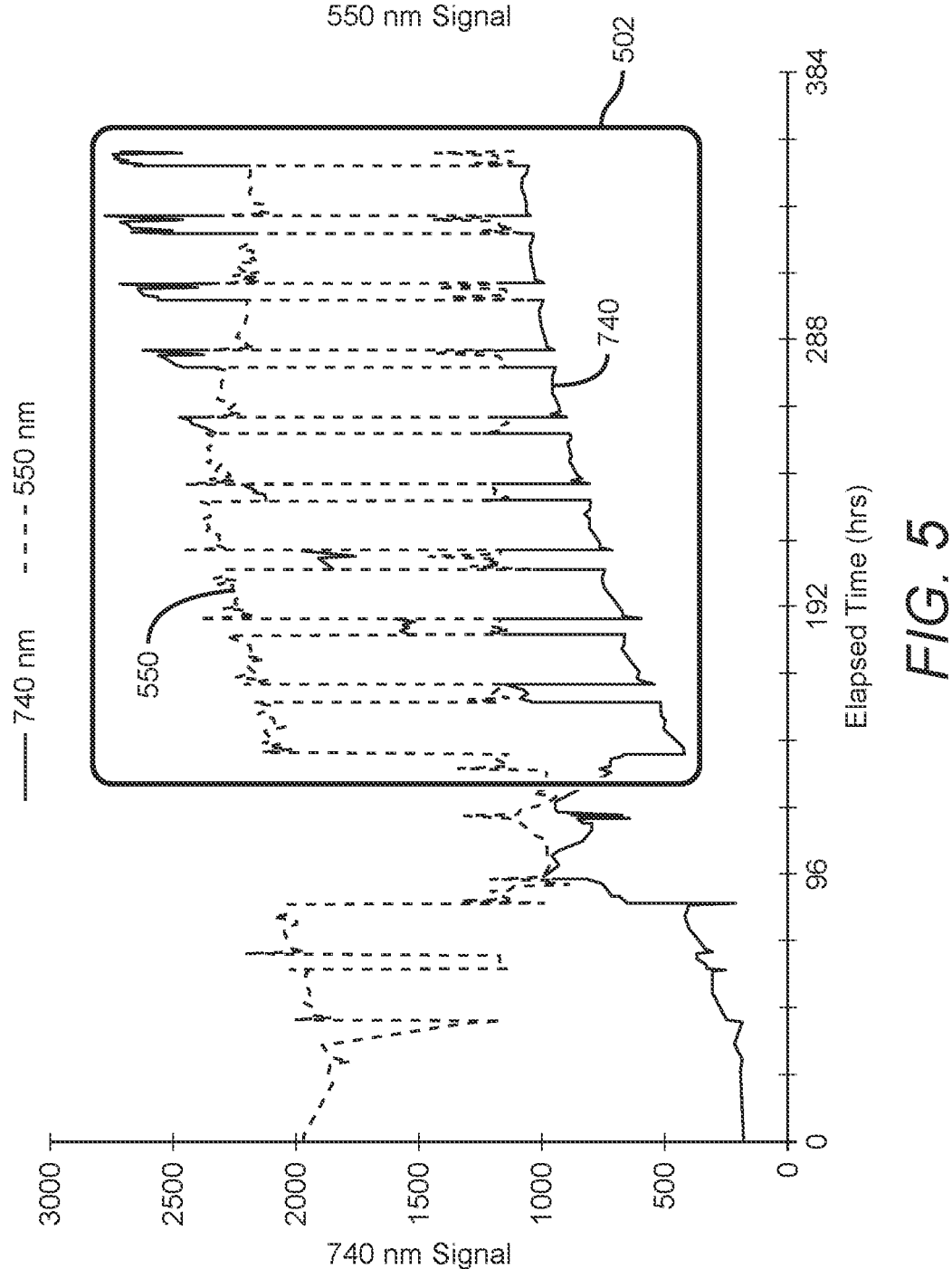
FIG. 5 plots observed chlorophyll fluorescence and green light reflectance over time for a plant species.

Under normal irrigation conditions, one would expect the ChIF and green reflectance signals to change in magnitude as a plant species grows and increases in size. For example, as the portion 502 of FIG. 5 illustrates, ChIF at 740 nm generally increases in magnitude as the plant species grows. Green reflectance tends to gradually increase with plant growth and may plateau or drop off slightly-generally staying within an expected range of values. As FIG. 3 illustrates, drought stress induced opposite signal trajectories for ChIF and green reflectance. In other words, ChIF at 740 nm decreased, while green reflectance increased. FIG. 4 is a bar graph that illustrates the magnitude and direction of change for ChIF and green reflectance under drought stress and recovery. When drought stress conditions were removed, ChIF and green reflectance signals resumed normal trajectories.

Visually observable plant wilting was detected approximately 12-14 hours after the signal responses 301 and 303, respectively—in other words, the signal response precedes visually observable conditions of drought stress. Observing the combination of ChIF and green reflectance provide a benefit to monitoring growth conditions and health of a plant species. Other stresses, such as temperature stress, may cause decreases in ChIF. Adding consideration of green reflectance and comparing the relative signal trajectories of ChIF and green reflectance provide a more accurate indicator of drought stress.

Example 2—High Temperature Stress

Figure 7:
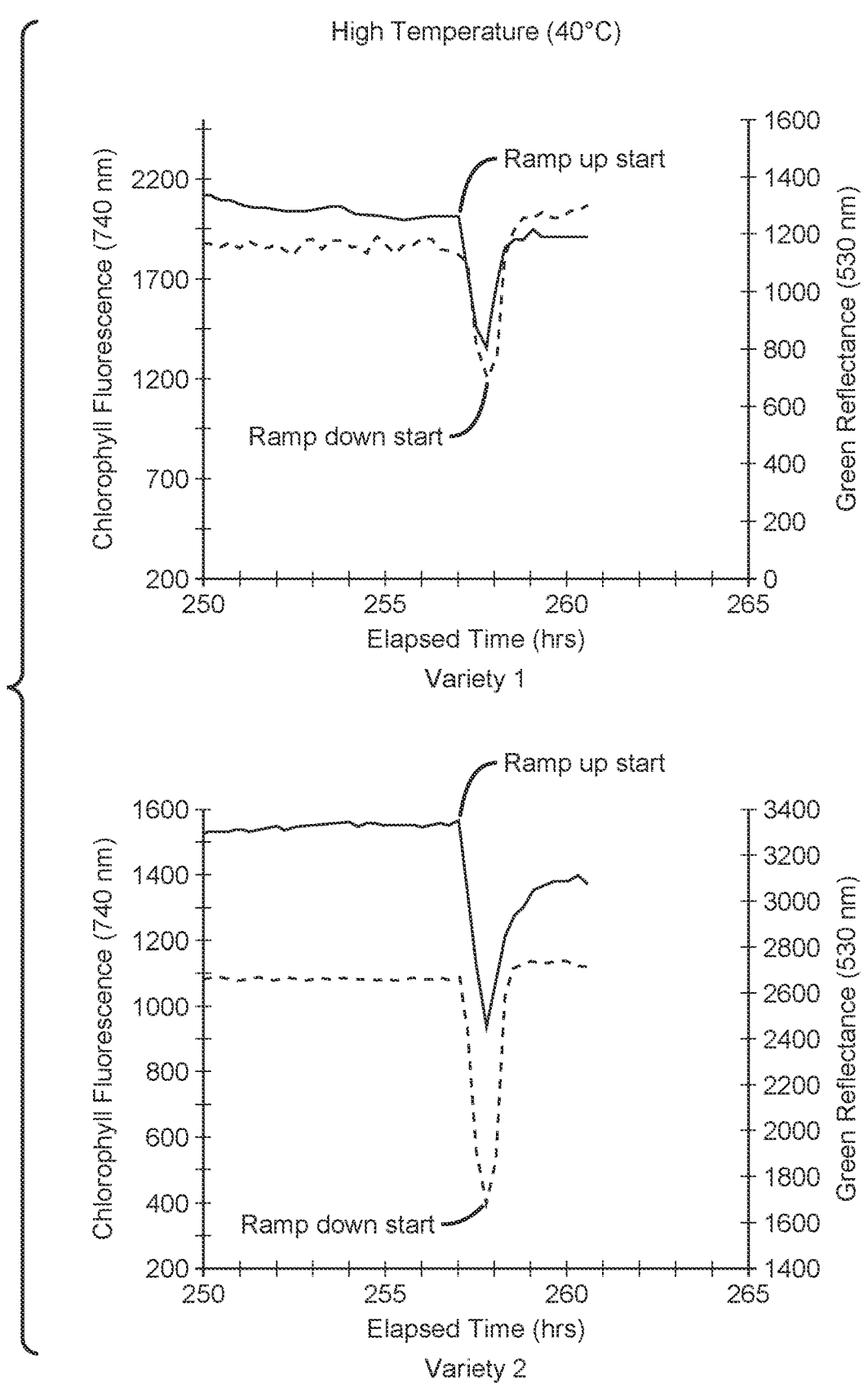
FIG. 7 plots observed chlorophyll fluorescence and green light reflectance over time for two plant species subjected to high temperature stress.

FIG. 7 includes two graphs that plot observed ChIF and green light reflectance over time for two plant varieties (a *Lactuca* variety (Variety 1) and a *Spinacia* variety (Variety 2)) growing under controlled environmental conditions, such as synthetic lighting and an automated irrigation system. As FIG. 7 illustrates, observed ChIF and green light reflectance deviated from signal patterns expected under normal growing conditions and moved in similar trajectories when subjected to temperature stress (here, 40 degrees C.). In particular, both signals decreased when subjected to temperature stress (ramp up start), and recovered when subjected to normal temperatures (ramp down start).

Example 3—Salinity (EC) Stress

Figure 8:
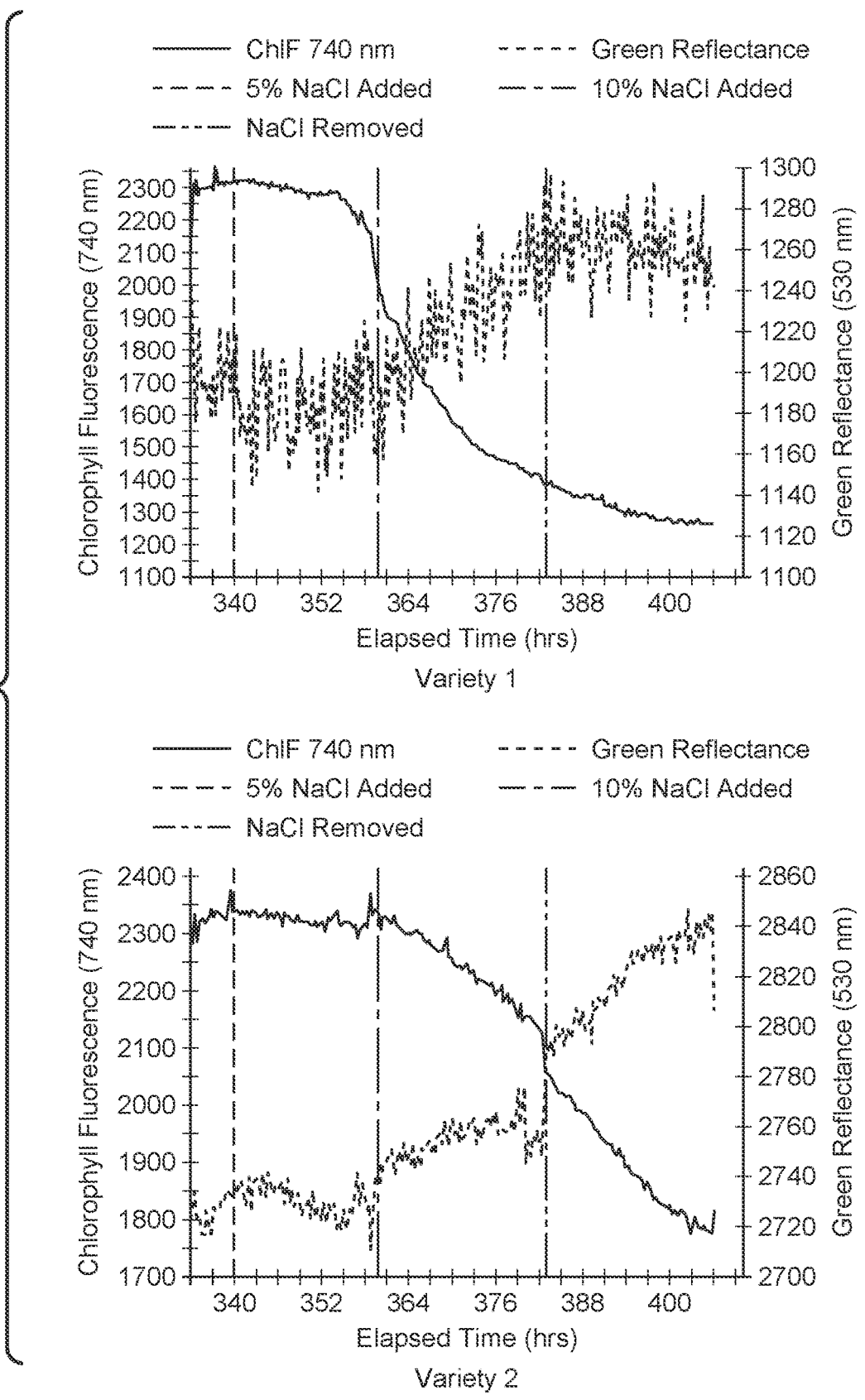
FIG. 8 plots observed chlorophyll fluorescence and green light reflectance over time for two plant species subjected salinity stress.

FIG. 8 includes two graphs that plot observed ChIF and green light reflectance over time for two plant varieties (Variety 1 and Variety 2, above) growing under controlled environmental conditions and subjected to salinity stress— i.e., irrigation with nutrient solution with a relatively high salt concentration. As FIG. 8 illustrates, observed ChIF and green light reflectance over time for the two plant varieties behaved similarly to drought stress conditions when subjected to salinity stress at 10% NaCl solution and recovered when the stress was removed. As FIG. 8 illustrates, the signal trends for ChIF and green light reflectance diverged when subjected to salinity stress. In FIG. 8, ChIF generally decreased, while green light reflectance increased upon increase in salinity.

Example 4—pH Stress

Figure 9:
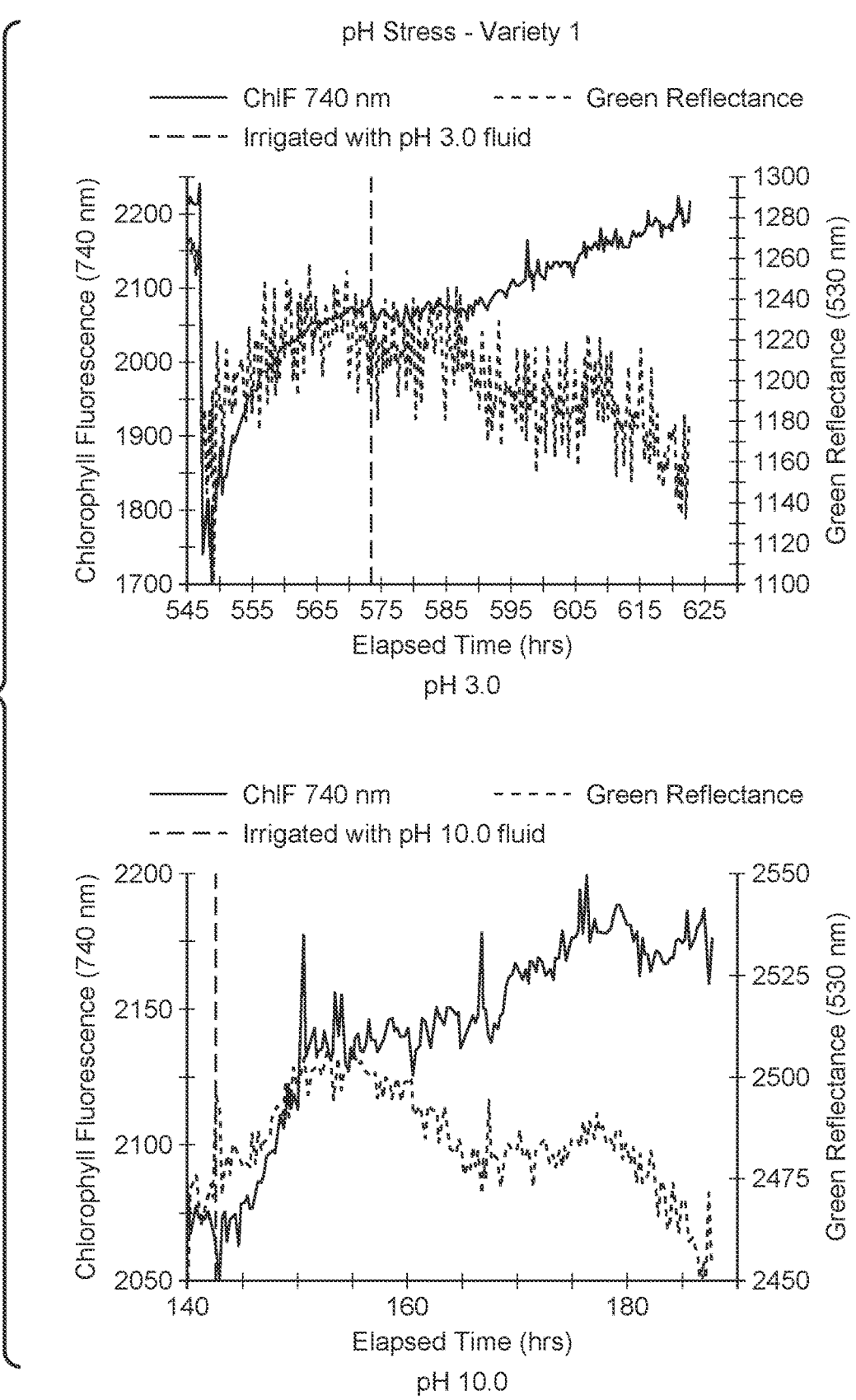
FIG. 9 plots observed chlorophyll fluorescence and green light reflectance over time for a plant species subjected pH stress.

FIG. 9 includes two graphs that plot observed ChIF and green light reflectance over time for Variety 1 growing under controlled environmental conditions and subjected to pH stress—i.e., irrigation with nutrient solution with a relatively high ($>=10$) and relatively low ($<=3$) pH levels. As FIG. 9 shows, observed ChIF and green light reflectance signal trends diverge after initiation of both low and high pH stress.

Example 5—Low Temperature Stress

Figure 10:
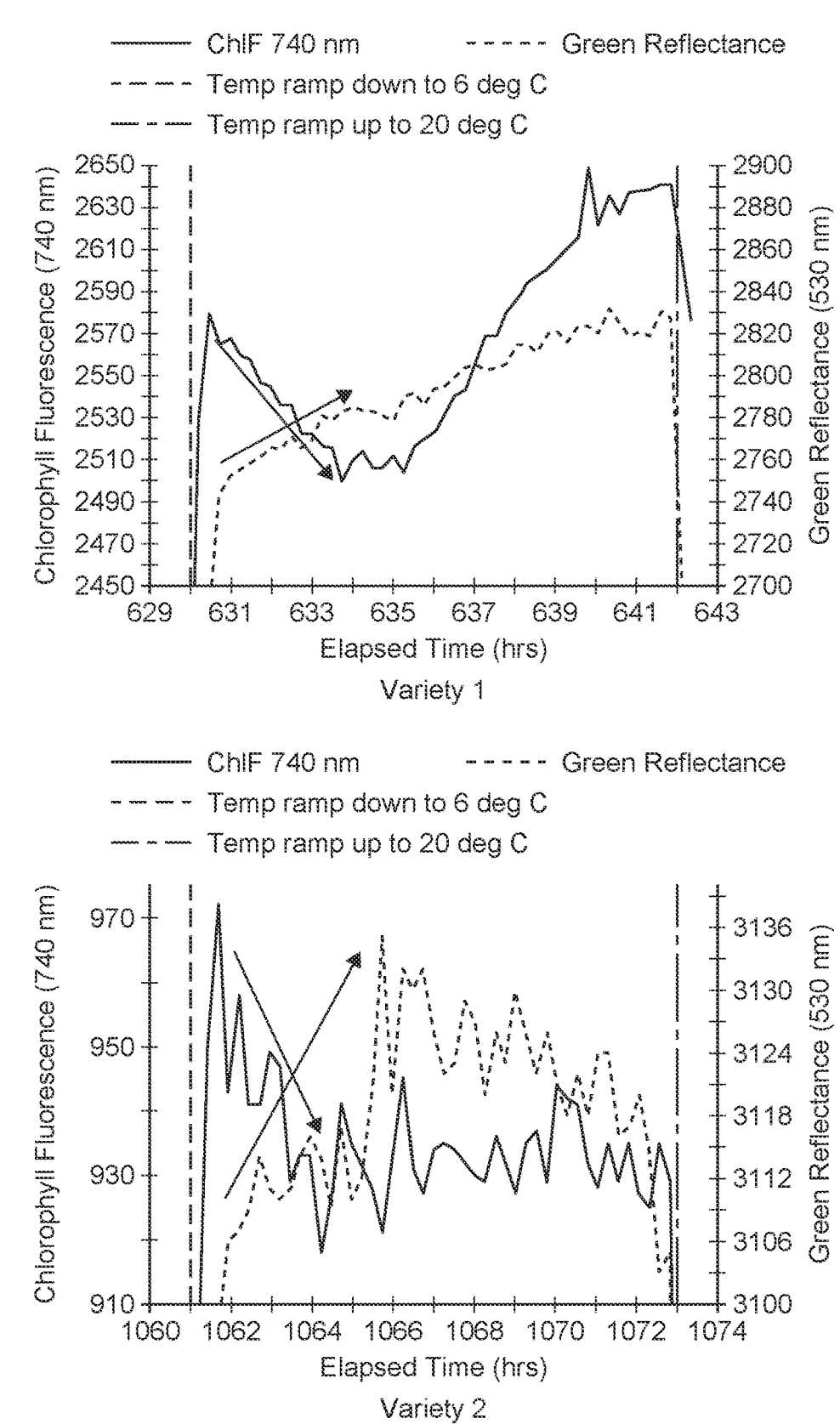
FIG. 10 plots observed chlorophyll fluorescence and green light reflectance over time for two plant species subjected to low temperature stress.

FIG. 10 includes two graphs that plot observed ChIF and green light reflectance over time for two plant varieties (Variety 1 and Variety 2, above) growing under controlled environmental conditions and subjected to low temperature stress. As FIG. 10 shows, observed ChIF and green light reflectance signal trends diverge after initiation of low temperature stress.

As shown above, an improved, non-destructive plant growth monitoring system can be created by experimentally inducing various types of stress conditions and observing ChIF and green light reflectance to develop data models that can be used to monitor plant growth in farm production systems. This diagnostic method may be configured to provide several advantages and uses in controlled environment agriculture. For example, a monitoring module may scan the ChIF and green reflectance signal data on a periodic interval and generate an alert when drought or other types of stress is detected. In one implementation, the monitoring module may periodically compare the slopes or trends of the ChIF and green reflectance signals and trigger a drought or other stress alert to a farm operator. For example, if the negative trend in the ChIF data is significant and lower than a threshold negative value and the positive trend in the green reflectance data is significant and higher than a threshold positive value, the monitoring module may trigger a drought stress alert. However, if the significant trends are both negative, the monitoring system may transmit an alert indicating a possible high temperature stress condition. In some implementations, windowing or data smoothing approaches could be used, such as weighted moving averages and the like. The triggered alert could indicate to the farm operator the need to check the farm system for potential irrigation or other system problems. If alerted early enough, the problem could be addressed before the permanent wilting point of the plant species, allowing for recovery of the stressed crop. In other implementations, machine learning techniques could be used to detect drought and other stresses. For example, a model could be constructed from ChIF data collected from plants grown under baseline growth conditions, drought stress conditions and other conditions. The monitoring module could be implemented as a series of instructions executed by the computing system hardware described in connection with FIG. 6. Still further, the drought stress alert could be used in closed-loop feedback control of lighting and other environmental parameters. For example, the drought stress alert could trigger a farm control system to turn off or lower the grow lights in and/or modify the flow of nutrient fluid to the area(s) corresponding to the alert in order to alleviate or reduce the stress.

Figure 11:
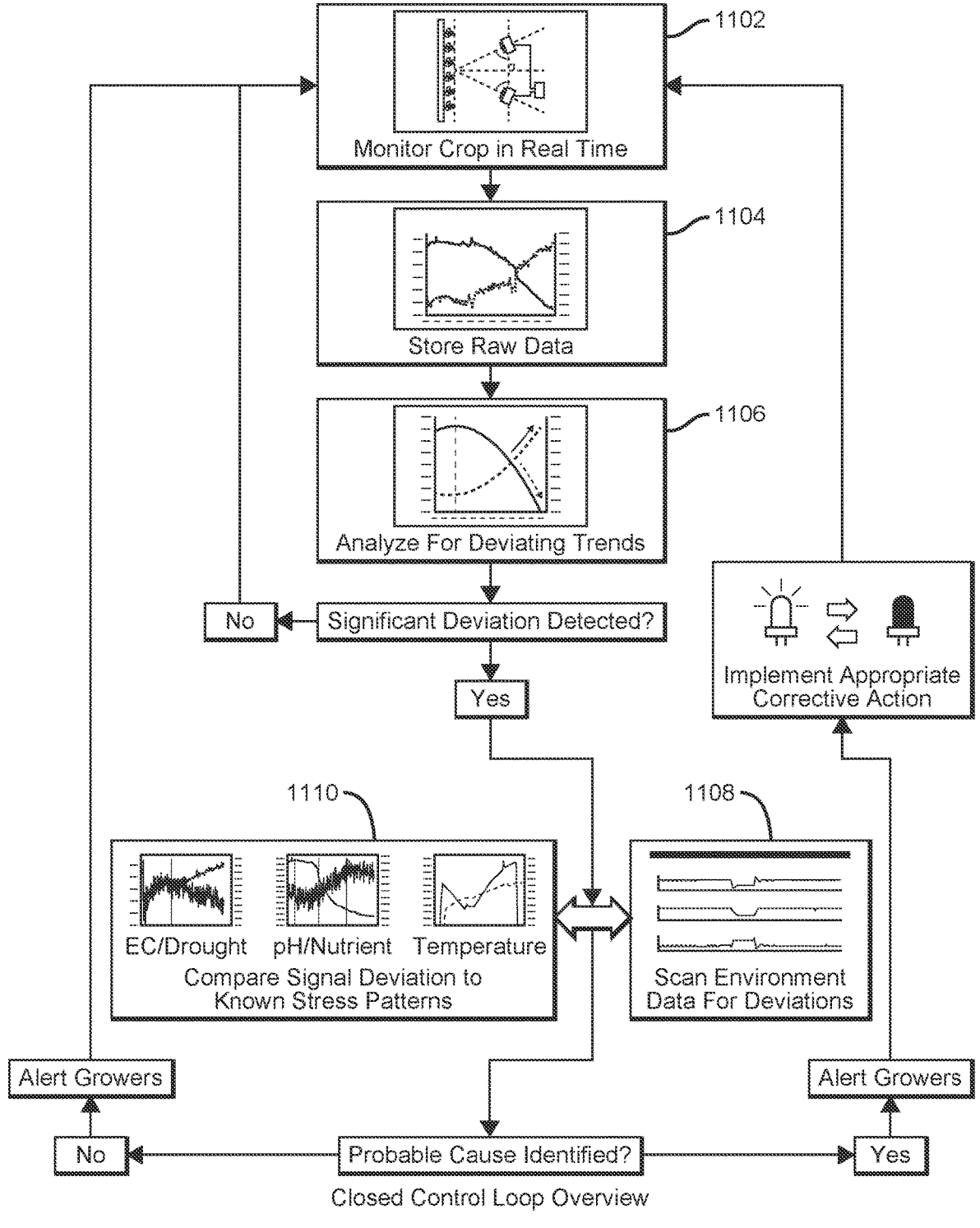
FIG. 11 is a flow chart illustrating a closed-loop control process according to one implementation of the invention.

FIG. 11 illustrates an example process flow for a closed loop control and alerting system that can be created under various implementations of the invention. As FIG. 11 shows, a farm system may employ system 100 to monitor ChIF and green light reflectance for crops in real time (1102) and record the data in a database (1104). A monitoring module may analyze the data for deviating trends (1106) on a periodic basis, such as every fifteen minutes or when new data is stored. In one implementation, monitoring module may use a statistics package to detect the significance of trends (e.g., assessing the second-order derivative of the signals) in the ChIF and green light reflectance signals. In one implementation, the statistics package can be the "trend" package, Version 1.1.4, "Non-Parametric Trend Tests and Change-Point Detection," authored by Thorsten Pohlert. If a significant deviation is detected, the monitoring module can scan environment data (e.g., temperature, humidity, etc.) (1108) and compare the signal deviation to known stress patterns (1110), such as drought stress, pH stress and the like. For example, the monitoring module may compare the direction and magnitude of significant trends in the signals to match to one or more known stress patterns. The monitoring module may also consider environmental data as part of this matching process. If a probable cause is identified, the monitoring module may also automatically trigger corrective action.

Figure 12:
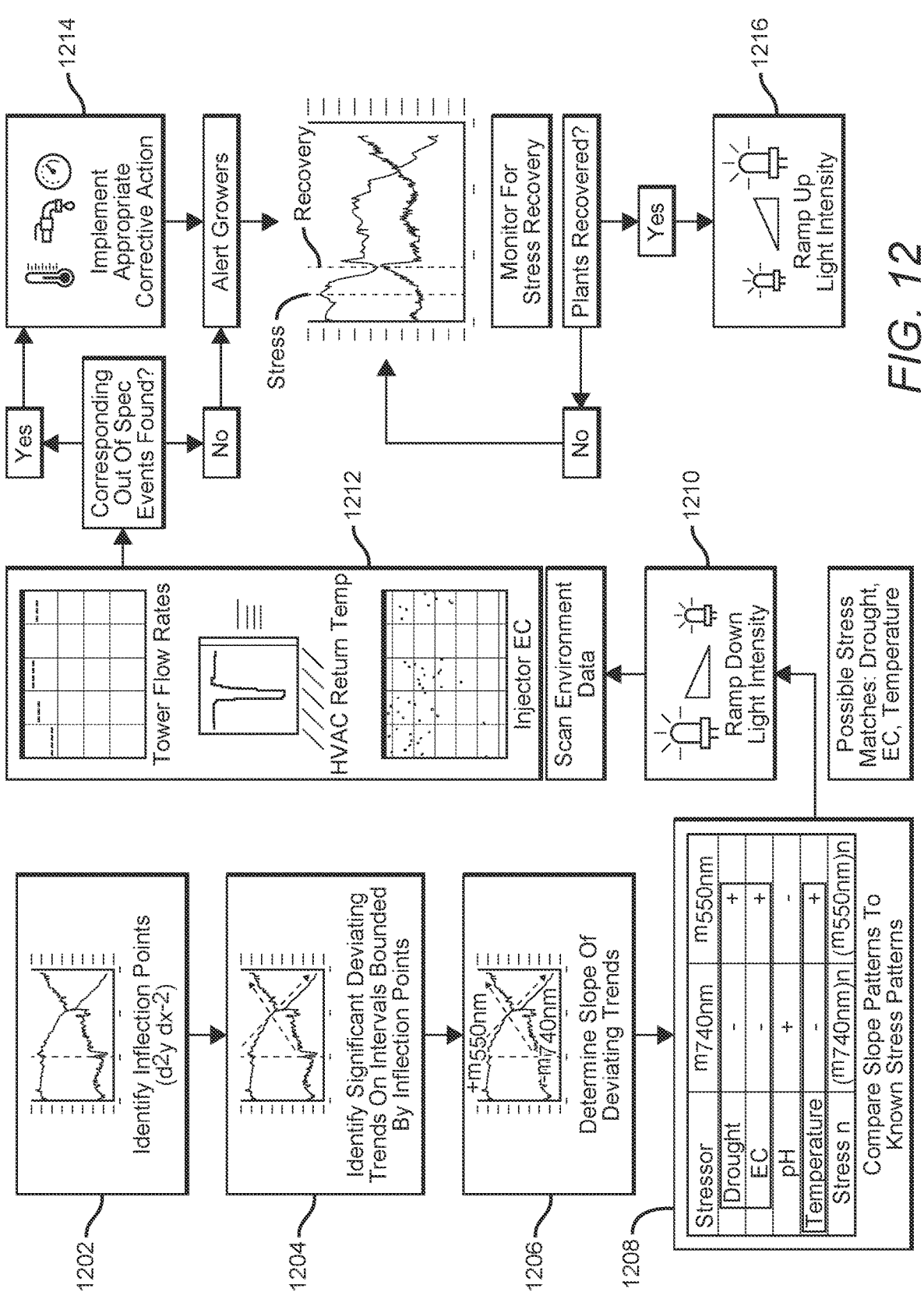
FIG. 12 a flow chart illustrating a closed-loop control process according to one implementation of the invention.

FIG. 12 provides an example process flow for detecting deviations in ChIF and green light reflectance and responding to identified stress conditions. The monitoring module may identify inflection points in the ChIF and green light reflectance signals (1202), identify significant deviating trends on intervals bounded by the inflection points (1204), and determine the slopes of the deviating trends (1206). In one implementation, if a significant deviating trend is detected by the monitoring module, it may compare the slopes of the ChIF and green light reflectance signals to known stress patterns to identify a potential stress (1208). Generally speaking, one would expect the signal trend to be positive during early stages of normal growth, with a progressively decreasing slope as the plants reach the stationary phase, eventually flattening to zero slope and possibly transitioning to a negative trend as the plants senesce. A negative deviating trend could be grounds for an alert signal, but whether or not monitoring module interprets it as such will depend on the results of the statistical trend analysis on data based on use of the system. If the results of such an analysis indicate that an inflection point followed by a downward trend are significant, relative to signal noise, then this might be a case where the monitoring module would issue an alert. If not, the changes would be interpreted as "noise" and not acted upon. As FIG. 12 shows, the monitoring module may also trigger an alert that causes the farm system to ramp down the intensity of the grow lights applied to the crop (1210), such as by 50 to 80 percent of normal specifications. The monitoring module may also scan environment data (1212) to possibly identify any grow conditions that may be out of specification, such as salinity of irrigation solution, temperature, or irrigation flow rates. If an out of specification condition is identified, the farm system may implementation corrective action (1214) and alert personnel. As FIG. 12 illustrates, the monitoring module may also monitor for conditions that suggest the crop has recovered, which may cause a ramp up of light intensity back to normal specifications (1216).

Other implementations are possible. For example, machine learning techniques may be used to train a model to detect stress conditions based on observed ChIF and green light reflectance. In some implementations, a depth camera could also be used to monitor for deviations to detect crop wilting. In addition, other data can be collected and used in the analysis, such as data from an RGB camera.

Figure 6:
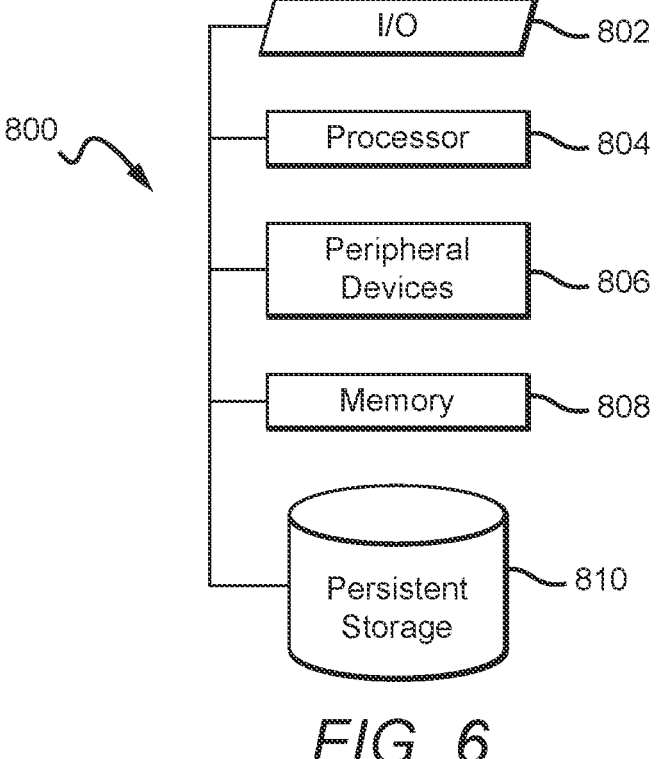
FIG. 6 illustrates an example of a computer system that may be used to execute instructions stored in a non-transitory computer readable medium (e.g., memory) in accordance with embodiments of the disclosure.

FIG. 6 illustrates an example of a computer system 800 that may be used to execute program code stored in a non-transitory computer readable medium (e.g., memory) in accordance with embodiments of the disclosure. The computer system includes an input/output subsystem 802, which may be used to interface with human users or other computer systems depending upon the application. The I/O subsystem 802 may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the controller 620, may be implemented with a computer system like that of computer system 800.

Program code may be stored in non-transitory media such as persistent storage in secondary memory 810 or main memory 808 or both. Main memory 808 may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors 804 reads program code from one or more non-transitory media and executes the code to enable the computer system to accomplish the methods performed by the embodiments herein. Those skilled in the art will understand that the processor(s) may ingest source code, and interpret or compile the source code into machine code that is understandable at the hardware gate level of the processor(s) 804. The processor(s) 804 may include graphics processing units (GPUs) for handling computationally intensive tasks.

The processor(s) 804 may communicate with external networks via one or more communications interfaces 807, such as a network interface card, WiFi transceiver, etc. A bus 805 communicatively couples the I/O subsystem 802, the processor(s) 804, peripheral devices 806, communications interfaces 807, memory 808, and persistent storage 810. Embodiments of the disclosure are not limited to this representative architecture. Alternative embodiments may employ different arrangements and types of components, e.g., separate buses for input-output components and memory subsystems.

Those skilled in the art will understand that some or all of the elements of embodiments of the disclosure, and their accompanying operations, may be implemented wholly or partially by one or more computer systems including one or more processors and one or more memory systems like those of computer system 800. In particular, the elements of automated systems or devices described herein may be computer-implemented. Some elements and functionality may be implemented locally and others may be implemented in a distributed fashion over a network through different servers, e.g., in client-server fashion, for example.

Additional operational and configuration details of an example farm system environment in which implementations can be used are set forth in International Application Serial Nos. PCT/US19/023201 and PCT/US19/058770, which are incorporated by reference herein for all purposes. In addition, while certain implementations are described as operating in connection with vertical grow towers, other implementations can be configured to monitor grow conditions in farm systems that employ other grow structures, such as horizontal trays stacked in vertical configurations, and the like.

Although the disclosure may not expressly disclose that some embodiments or features described herein may be combined with other embodiments or features described herein, this disclosure should be read to describe any such combinations that would be practicable by one of ordinary skill in the art. Unless otherwise indicated herein, the term "include" shall mean "include, without limitation," and the term "or" shall mean non-exclusive "or" in the manner of "and/or."

Those skilled in the art will recognize that, in some embodiments, some of the operations described herein may be performed by human implementation, or through a combination of automated and manual means. When an operation is not fully automated, appropriate components of embodiments of the disclosure may, for example, receive the results of human performance of the operations rather than generate results through its own operational capabilities.

All references, articles, publications, patents, patent publications, and patent applications cited herein are incorporated by reference in their entireties for all purposes to the extent they are not inconsistent with embodiments of the disclosure expressly described herein. However, mention of any reference, article, publication, patent, patent publication, and patent application cited herein is not, and should not be taken as an acknowledgment or any form of suggestion that they constitute valid prior art or form part of the common general knowledge in any country in the world, or that they are disclose essential matter.

What is claimed is:

1. An apparatus for monitoring one or more growing conditions of a plant, comprising:

a controller;

one or more excitation light sources operably connected to the controller, each of the excitation light sources operable to emit an excitation light in response to an excitation control signal transmitted by the controller, the excitation light having an emitted light spectrum operable to induce chlorophyll fluorescence ("ChIF") from a plant species;

a detection module operably connected to the controller and comprising a first photodetector operable to detect an amount of excited ChIF light from the plant species and convert the detected excited ChIF light into an excited detection electrical signal, the excited ChIF light emitted from the plant species in response to receiving the excitation light;

a second photodetector operable to detect an amount of green light reflected from the plant species and convert the detected reflected green light into a reflected detection electrical signal, the reflected green light emitted from the plant species in response to ambient or controlled lighting conditions;

wherein the controller is operable to determine chlorophyll fluorescence data based, at least in part, on the excited detection electrical signal;

determine green light reflectance data based, at least in part, on the reflected detection electrical signal;

cause the one or more excitation light sources and the detection module to repeat detecting of ChIF and green light reflectance at periodic intervals; and a computing system programmed to detect one or more plant stress conditions of the plant species based on monitoring of the ChIF and green light reflectance detected over an analysis period by determining a first signal trajectory of the ChIF detected over the analysis period;

determining a second signal trajectory of the green light reflectance detected over the analysis period;

mapping the first and second signal trajectories against one or more combinations of reference signal trajectories, wherein each of the one or more combinations of reference signal trajectories includes a reference signal trajectory for ChIF and a reference signal trajectory for green light reflectance and corresponds to a plant stress condition of the one or more plant stress conditions; and selecting the plant stress condition from the one or more plant stress conditions based on the mapping the first and second signal trajectories against the one or more combinations of reference signal trajectories, wherein a first plant stress condition of the one or more plant stress conditions comprises drought stress, and wherein the combination of signal trajectories associated with the first plant stress condition comprises a reference signal trajectory for ChIF that diverges from the reference signal trajectory for green light reflectance, and a second plant stress condition of the one or more plant stress conditions comprises high temperature stress, and wherein the combination of signal trajectories associated with the second plant stress condition comprises a reference signal trajectory for ChIF that follows the reference signal trajectory for green light reflectance.

2. The apparatus of claim 1 wherein the computing system is programmed to generate an alert in response to detection of a plant stress condition from the one or more plant stress conditions.

3. The apparatus of claim 1 wherein the excitation light source is a light emitting diode.

4. The apparatus of claim 3 wherein the excitation control signal is operable to cause the at least one excitation light source to emit light for a target pulse duration and at a target frequency and duty cycle.

5. The apparatus of claim 4 wherein the detection module is operable to filter the excited detection electrical signal based on the target frequency.

6. The apparatus of claim 1 wherein the computing system is operable to modulate one or more environmental growing control parameters for the plant species in response to detecting at least one of the one or more growth conditions.

7. The apparatus of claim 6 wherein the computing system is programmed to lower an intensity of one or more grow lights in response to detecting a plant stress condition of the one or more plant stress conditions.

8. The apparatus of claim 1 wherein the first photodetector is operable to detect light emitted at a 740 nanometer wavelength.

9. The apparatus of claim 8 wherein the excitation light source is a light emitting diode.

10. The apparatus of claim 1 wherein the second photodetector is operable to detect light emitted at a 550 nanometer wavelength.

11. The apparatus of claim 1 wherein for the second plant stress condition the reference signal trajectory for ChIF and the reference signal trajectory for green light reflectance are both downward signal trajectories.

12. An apparatus for monitoring one or more growing conditions of a plant, comprising:

a controller;

one or more excitation light sources operably connected to the controller, each of the excitation light sources operable to emit an excitation light in response to an excitation control signal transmitted by the controller, the excitation light having an emitted light spectrum operable to induce chlorophyll fluorescence ("ChIF") from a plant species;

a detection module operably connected to the controller and comprising a first photodetector operable to detect an amount of excited ChIF light from the plant species and convert the detected excited ChIF light into an excited detection electrical signal, the excited ChIF light emitted from the plant species in response to receiving the excitation light;

a second photodetector operable to detect an amount of green light reflected from the plant species and convert the detected reflected green light into a reflected detection electrical signal, the reflected green light emitted from the plant species in response to ambient or controlled lighting conditions;

wherein the controller is operable to determine chlorophyll fluorescence data based, at least in part, on the excited detection electrical signal;

determine green light reflectance data based, at least in part, on the reflected detection electrical signal;

cause the one or more excitation light sources and the detection module to repeat detecting of ChIF and green light reflectance at periodic intervals; and a computing system programmed to detect one or more plant stress conditions of the plant species based on monitoring of the ChIF and green light reflectance detected over an analysis period by determining a first signal trajectory of the ChIF detected over the analysis period;

determining a second signal trajectory of the green light reflectance detected over the analysis period;

mapping the first and second signal trajectories against one or more combinations of reference signal trajectories, wherein each of the one or more combinations of reference signal trajectories includes a reference signal trajectory for ChIF and a reference signal trajectory for green light reflectance and corresponds to a plant stress condition of the one or more plant stress conditions; and selecting the plant stress condition from the one or more plant stress conditions based on the mapping the first and second signal trajectories against the one or more combinations of reference signal trajectories, wherein a first plant stress condition of the one or more plant stress conditions comprises drought stress, and wherein the combination of signal trajectories associated with the first plant stress condition comprises a reference signal trajectory for ChIF that diverges from the reference signal trajectory for green light reflectance, and the reference signal trajectory for ChIF is a downward signal trajectory and the reference signal trajectory for green light reflectance is an upward signal trajectory.

* * * * *